(12) United States Patent
Pan et al.

(10) Patent No.: US 10,523,036 B2
(45) Date of Patent: Dec. 31, 2019

(54) RESONANT WIRELESS CHARGING SYSTEM AND METHOD FOR ELECTRIC TOOTHBRUSH

(71) Applicant: Shenzhen Yichong Wireless Power Technology Co. Ltd., Shenzhen, Guangdong (CN)

(72) Inventors: Siming Pan, San Jose, CA (US); Tun Li, San Jose, CA (US); Dawei He, Burlingame, CA (US)

(73) Assignee: SHENZHEN YICHONG WIRELESS POWER TECHNOLOGY CO. LTD, Shenzhen (CN)

( * ) Notice: Subject to any disclaimer, the term of this patent is extended or adjusted under 35 U.S.C. 154(b) by 0 days.

(21) Appl. No.: 15/378,607

(22) Filed: Dec. 14, 2016

(65) Prior Publication Data
US 2018/0166904 A1 Jun. 14, 2018

(51) Int. Cl.
*H02J 7/02* (2016.01)
*A61C 17/22* (2006.01)

(52) U.S. Cl.
CPC ............ *H02J 7/025* (2013.01); *A61C 17/224* (2013.01)

(58) Field of Classification Search
CPC ........ H02J 7/025; H02J 7/0044; A61C 17/224
USPC .......................................... 320/108, 115, 162
See application file for complete search history.

(56) References Cited

U.S. PATENT DOCUMENTS

| | | |
|---|---|---|
| 6,501,364 B1 | 12/2002 | Hui et al. |
| 6,888,438 B2 | 5/2005 | Hui et al. |
| 7,164,255 B2 | 1/2007 | Hui |
| 7,495,414 B2 | 2/2009 | Hui |
| 7,576,514 B2 | 8/2009 | Hui |
| 7,855,529 B2 | 12/2010 | Liu |
| 7,872,445 B2 | 1/2011 | Hui |
| 7,915,858 B2 | 3/2011 | Liu et al. |
| 8,040,103 B2 | 10/2011 | Hui et al. |
| 8,228,025 B2 | 7/2012 | Ho et al. |
| 8,269,456 B2 | 9/2012 | Hui |
| 8,290,463 B2 | 10/2012 | Liu et al. |
| 8,294,418 B2 | 10/2012 | Hui et al. |
| 8,299,753 B2 | 10/2012 | Hui |
| 8,300,440 B2 | 10/2012 | Ho et al. |
| 8,301,077 B2 | 10/2012 | Xue et al. |
| 8,519,668 B2 | 8/2013 | Hui |
| 8,554,165 B2 | 10/2013 | Liu et al. |
| 8,624,545 B2 | 1/2014 | Hui et al. |
| 8,711,593 B2 | 4/2014 | Ho et al. |
| 8,823,318 B2 | 9/2014 | Liu et al. |

(Continued)

FOREIGN PATENT DOCUMENTS

| | | |
|---|---|---|
| CN | 101243593 B | 6/2011 |
| CN | 101228678 B | 5/2012 |

(Continued)

*Primary Examiner* — Edward Tso
*Assistant Examiner* — Aaron Piggush
(74) *Attorney, Agent, or Firm* — Sheppard Mullin Richter & Hampton LLP

(57) ABSTRACT

A system for wireless electrical charging is disclosed. The system may comprise a charging station and one or more electric devices. The charging station may comprise an input node configured to receive a power input, and a transmitter resonant circuit including a transmitter coupling coil configured to oscillate at a resonant frequency. The one or more electric devices may comprise a receiver resonant circuit including a receiver coupling coil wirelessly coupled to the transmitter coupling coil, and a DC voltage charger configured to charge one or more batteries in the electric device.

16 Claims, 7 Drawing Sheets

(56) References Cited

U.S. PATENT DOCUMENTS

| | | |
|---|---|---|
| 8,836,171 B2 | 9/2014 | Choi et al. |
| 8,917,057 B2 | 12/2014 | Hui |
| 8,942,018 B2 | 1/2015 | Ho et al. |
| 9,087,345 B2 | 7/2015 | Liu et al. |
| 9,178,361 B2 | 11/2015 | Liu et al. |
| 9,281,720 B2 | 3/2016 | Liu |
| 9,438,315 B2 | 9/2016 | Swaans et al. |
| 9,825,486 B2 | 11/2017 | Liu et al. |
| 9,973,239 B2 | 5/2018 | Liu et al. |
| 10,044,233 B2 | 8/2018 | Liu et al. |
| 2009/0096413 A1* | 4/2009 | Partovi ............ H02J 7/025 320/108 |
| 2016/0322852 A1* | 11/2016 | Yeh ............ H02J 7/025 |

FOREIGN PATENT DOCUMENTS

| | | |
|---|---|---|
| CN | 101630861 B | 3/2013 |
| CN | 101971458 B | 8/2013 |
| CN | 102742138 B | 8/2014 |
| CN | 102714348 B | 10/2014 |
| CN | 102687339 B | 1/2015 |
| CN | 102088210 B | 5/2015 |
| CN | 102124640 B | 6/2015 |
| CN | 103907264 B | 6/2015 |
| CN | 102246405 B | 6/2016 |
| CN | 104685760 B | 11/2016 |
| CN | 103765960 B | 5/2018 |
| EP | 1908159 B1 | 1/2014 |
| EP | 1915809 B1 | 7/2014 |
| EP | 2146414 B1 | 9/2014 |
| EP | 2321894 B1 | 7/2016 |
| EP | 2685594 B1 | 11/2017 |
| EP | 2479866 B1 | 7/2018 |
| GB | 2389720 B | 9/2005 |
| GB | 2399466 B | 11/2005 |
| GB | 2389767 B | 4/2006 |
| WO | 2013/013564 A1 | 1/2013 |

* cited by examiner

RESONANT WIRELESS CHARGING SYSTEM AND METHOD FOR ELECTRIC TOOTHBRUSH

TECHNICAL FIELD

The present disclosure relates generally to methods and systems for wirelessly charging devices, and more particularly, to methods and systems for wirelessly charging an electric tooth-brush.

BACKGROUND

Placement of different chargeable electric devices on typical charging stations requires rigid and careful handling to ensure coupling between the device and the charging station. Such rigid arrangements for charging work only for a single dedicated device at a time. Children, seniors or people with disabilities may find such devices difficult to work with. Further, wireless charging arrangements may have a limited charging area that has built-in inflexibility in the electric device placement. More than one electric device cannot be charged at the same time.

Chargeable electric devices come in all shapes and sizes. For example, an electric toothbrush uses commonly rechargeable or replaceable batteries. A charging station used with an electric toothbrush would have to consider water resistance and electrical safety issues. The batteries of modern electric toothbrushes are usually hermetically sealed inside of the handle and can be recharged through inductive wireless charging when the toothbrush sits in the charging base. Such arrangements have limited charging areas, require inflexible placement of toothbrush, and require a dedicated charging transmitter that is unable to charge more than one toothbrush at a time. Even available special charging bases require precise fixing of the toothbrush's position for wireless charging.

SUMMARY

One aspect of the present disclosure is directed to a system for charging one or more electric devices. The system may comprise of a charging station and one or more electric devices. The charging station may comprise an input node configured to receive a power input, and a transmitter resonant circuit including a transmitter coupling coil configured to oscillate at a resonant frequency. The one or more electric devices may comprise a receiver resonant circuit including a receiver coupling coil wirelessly coupled to the transmitter coupling coil, and a DC voltage charger configured to charge one or more batteries in the electric device.

Another aspect of the present disclosure is directed to a method for charging one or more electric devices. The method may comprise receiving a power input by a charging station, oscillating a transmitter resonant circuit of the charging station at a resonant frequency, and wirelessly coupling the transmitter resonant circuit to a receiver resonant circuit of the one or more electric devices.

It is to be understood that the foregoing general description and the following detailed description are exemplary and explanatory only, and are not restrictive of the invention, as claimed.

BRIEF DESCRIPTION OF THE DRAWINGS

The accompanying drawings, which constitute a part of this disclosure, illustrate several embodiments and, together with the description, serve to explain the disclosed principles.

DETAILED DESCRIPTION

Reference will now be made in detail to exemplary embodiments, examples of which are illustrated in the accompanying drawings. The following description refers to the accompanying drawings in which the same numbers in different drawings represent the same or similar elements unless otherwise represented. The implementations set forth in the following description of exemplary embodiments consistent with the present invention do not represent all implementations consistent with the invention. Instead, they are merely examples of systems and methods consistent with aspects related to the invention.

Wireless charging stations for different size and shapes of electric devices are designed for specific devices and dedicated to a single device at a time. The mechanical or electrical coupling to charge such devices is inflexible. The disclosed systems and methods may mitigate or overcome one or more of the problems set forth above and/or other problems in the prior art.

Figure 1:
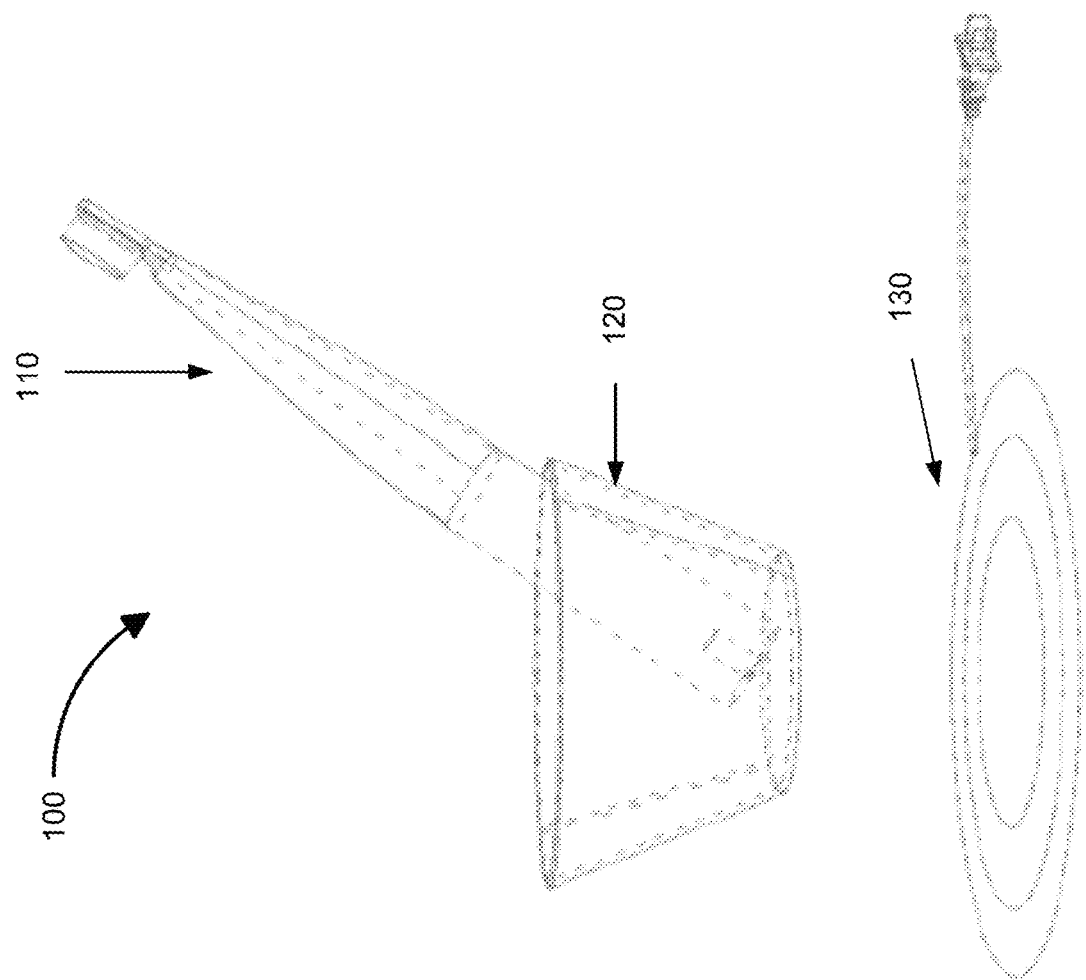
FIG. 1 is a graphical representation illustrating a holder that allows more than one toothbrushes to be placed in it with a flexible distance and angle from the charging base station, consistent with exemplary embodiments of the present disclosure.

FIG. 1 is a graphical representation 100 illustrating an electric device 110 that may be placed in a free position in a cup holder 120 that would be placed on the uniform charging plate 130, consistent with exemplary embodiments of the present disclosure. Though FIG. 1 illustrates one cup holder and one toothbrush, a person of ordinary skill of art would appreciate charging plate 130 working for multiple electric devices in multiple cup holders, as long as charging plate 130 has a sufficiently large area. The electric device 110 in this example is an electric toothbrush. A person of ordinary skill in the art would understand that the electric device 110 may have a shape, size and/or angular body different from that of the electric toothbrush shown in FIG. 1. Electric device 110 may also embody other types of electrical devices that include one or more chargeable or replaceable batteries. Electric device 110 may be a Bluetooth device, a near field communication device or radio frequency identification device or any internet of things device.

The cup holder 120 may hold more than one electric device 110. The cup holder 120 may be made of glass or plastic materials. In certain embodiments, the cup holder may be of any shape that would allow holding different electrical devices. The cup holder 120 may be a cup that is routinely available in a household and need not be specifically designed to work with the wireless charging station shown in the graphical representation 100. For example, the inner surface of the cup does not need to have a special design to hold the toothbrush in fixed positions inside the cup. In FIG. 1, the round uniform plate with the wireless charging station 130 is shown to be separate and distinct from the cup holder. In certain embodiments, the round uniform plate with the wireless charging station 130 may connected permanently with the base of the cup holder 120. In certain embodiments, the wireless charging station 130 may be disposed on the cup holder 120, and can be moved or removed freely.

As illustrated in FIG. 1, electric device 110 is in a free position. Electric device 110 each time may be placed in a different position in the cup holder. There is no special mechanical coupling between the bottom of the electric device and the base of the cup holder. The cup or holder implemented in the disclosed embodiments can be a non-specially designed cup or holder. In certain embodiments, the electric device 110 is at an angle from the base of the cup holder 120. In certain embodiments, the electric device 110 is resting at an angle between 0 and 30 degrees to the base of the cup holder. The position of the electric device 110 in FIG. 1 is merely illustrative. In certain embodiments, the distance between the bottom of the electric device 110 and the wireless charging station 130, e.g., a charging range, can vary from 1 cm to 10 cm. In some embodiments, the cup holder 120 may be optional or may be replaced by an alternative object, as long as the electric device 110 is within the charging range of the wireless charging station 130.

In certain embodiments, one or more electric devices placed in the cup holder 120 may be detected through various methods. In one method, the wireless charging station 130 may include a sensor, e.g., camera, weight sensor, and the like, that detects whether there are one or more electric devices 110 placed in a cup holder 120 for charging. Based on whether an electric device 110 is sensed, the wireless charging station 130 may enable or disable the charging circuit allowing for efficient power consumption. Alternatively, the sensor may be independent of the wireless charging station 130. In another method, the wireless charging station 130 may monitor an input current of itself, based on which the wireless charging station 130 can determine whether one or more electric devices have been placed in proximity for charging. For example, if the wireless charging station 130 detects a change in the input current, depending on if it is a positive or negative change, it may determine the addition or removal of an electric device.

Figure 2:
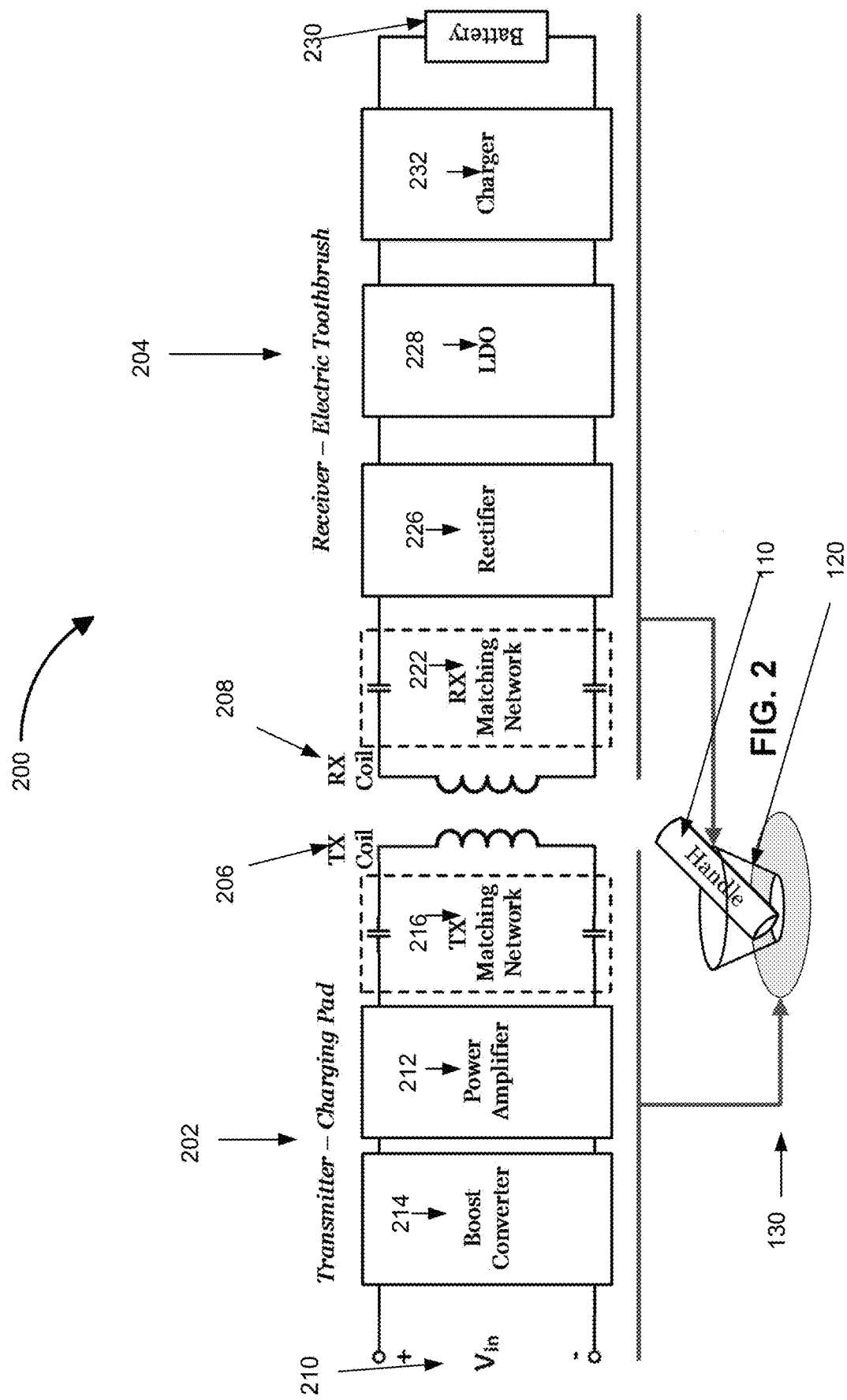
FIG. 2 is a diagram of a wireless charging system showing transmitter and receiver, consistent with exemplary embodiments of the present disclosure.

FIG. 2 shows a wireless charging system 200, consistent with exemplary embodiments of the present disclosure. As shown in FIG. 2, the wireless charging system 200 includes a transmitter side 202 and a receiver side 204. The transmitter side 202 and receiver side 204 are coupled by inductors 206,208 there between. In one exemplary embodiment, the transmitter side 202 includes voltage input nodes (+ and −) 210, a boost converter 214, a power amplifier 212 and a transmitter matching network 216. The receiver side 204 includes a receiver matching network 222, a rectifier 226, a low dropout regulator (LDO) 228, a charger 232 and a battery 230. The transmitter side 202 may be implemented in a charging device or a charging station. The receiver side 204 may be implemented in a consumer electronic device, such as a cell phone, headset, watch, tablet device, laptop, electronic brush, electric toothbrush, car, or any other consumer electronic devices that may be wirelessly charged. Alternatively, the transmitter side may be implemented as a stand-alone charging device for a user to attach a consumer electronic device. For example, a user can attach the chargeable battery portion of an electronic device as the battery 230 as shown in FIG. 2.

As shown in FIG. 2, the input nodes receive an input voltage Vin 210. In certain embodiments, the input voltage Vin 210 may be 5 volts provided through a USB port. The input nodes are connected to a boost converter 214. The boost converter 214 can provide a range of the DC voltage that can be feed into the power amplifier. For example, the boost converter 214 may be a step up converter that converts the Vin 210 from 5 volts to 12 volts. The output of the boost converter 214 feeds the power amplifier 212, which amplifies the input voltage Vin. The power amplifier 212 is connected to the TX matching network 216. The TX matching network 216 is connected to the inductor 206. The TX matching network 216 may include one or more capacitors. Capacitance of one or more of the capacitors may be adjustable. The TX matching network 216 and the inductor 206 form a resonant circuit or an LC circuit where the L represents the inductor and C represents the capacitor connected together. The frequency of the LC circuit can be adjusted by adjusting the capacitance of the TX matching network 216. The inductor 206 transmits the energy to the inductor 208 on the receiver side 204.

On the receiver side 204, similar to the transmitter side 202, the inductor 208 is connected to the RX matching network 222, which has one or more capacitors. One or more of the capacitors may have adjustable capacitance. The capacitors are used to adjust the frequency of an LC circuit formed by the inductor 208 and RX matching network 222 to match the LC circuit on the transmitter side 202. Accordingly, the resonant frequency of the LC circuit can be determined by tuning the capacitance and inductance and/or by accurately choosing the capacitor and the inductor. In certain embodiments, the transmitter 202 and the receiver 204 may be specially configured to have 1 to 10 MHz high resonant frequency (e.g., 6.78 MHz). Since the TX coil 206 and the RX coil 208 are magnetically coupled, oscillations in the transmitter 202 may induce electromotive forces in the receiver 294.

In some situations, the mutual inductance between the TX and RX coils may decrease when the coil size difference is large or two coils are not closely coupled with each other, and the wireless charging effect can be adversely affected. This is could be a reason why traditional wirelessly charging toothbrushes are usually disposed on a matching base in a fixed position to ensure the maximum coil coupling. In comparison, with the 1 to 10 MHz, e.g., the 6.78 MHz, resonant frequency of wireless power, the wireless charging system 200 can maintain good charging efficiency even when the mutual inductance decreases. In addition, with an optimization algorithm described below with reference to FIG. 7 in system level, the wireless charging system 200 can provide a large universal wireless charging area for electrical toothbrush and allow free positioning with tilted angles. For example, the charging distance between the TX coil and the RX coil may be as large as 10 cm, and the tilted angle may be as large as 30 degrees.

The underlying reasons and benefits for applying the high resonant frequency is disclosed below. To achieve the best power transfer efficiency between an inductively coupled transmitter circuit and a receiver circuit, in some exemplary embodiments, the operation frequency $\omega$ of the resonant circuit of system 200 is the resonant frequency $\omega_0$ and equals to $2\pi f_0$. Under this condition, the power transfer efficiency $\eta$ can be represented as:

$$\eta = \frac{P_2}{P_1}$$

$$= \frac{\omega_0^2 M^2 R_L}{R_1(R_L + R_2)^2 + \omega_0^2 M^2(R_L + R_2)},$$

where $P_1$ is the transmitter power, $P_2$ is the receiver power, $\omega = \omega_0 = 1/\sqrt{L_2 C_2}$, $X_L = 0$, M is the mutual inductance between the transmitter and receiver circuit, which is $k\sqrt{L_1 L_2}$, $L_1$ is transmitter coil inductance, $L_2$ is receiver coil inductance, k is the coupling coefficient, $C_1$ is transmitter capacitance, $C_2$ is receiver capacitance, $R_1$ is transmitter resistor resistance, $R_2$ is receiver resistor resistance, and $R_L$ is the real part of the impedance of the receiver circuit.

The above power transfer efficiency can be further simplified to:

$$\eta = \frac{(\omega_0 M)^2 R_L}{Z_2((\omega_0 M)^2 + Z_1 Z_2)} \times 100\%,$$

where $Z_1 = R_1$, $Z_2 = R_L + R_2$. In a weakly or loosely coupled wireless power transfer system where the transmitter resonant circuit is loosely coupled to the receiver resonant circuit, for example, when the toothbrush is shifted in position and not perfectly coupling to the charger coil, the coupling coefficient k is small (e.g., 0.02<k<0.1), so: $2R_1 R_2 \gg \omega_0^2 M^2$, and the above efficiency equation can be further simplified to:

$$\eta = \frac{P_2}{P_1} \cong \frac{\omega_0^2 M^2}{4 R_1 R_2} \text{(weak coupling)},$$

where mutual inductance M is $k\sqrt{L_1 L_2}$, and k is the coupling factor. Therefore, in order to maximize the power transfer efficiency η, with fixed $R_1$, $R_2$, and M, the resonant frequency $\omega = \omega_0$ needs to be high (e.g., w in the order of MHz, $L_2 C_2 < 4\pi^2$ MHz$^{-2}$ if $\omega > 1$ MHz), particularly in weakly (loosely) coupled wireless power transfer system.

The RX matching network 222, is connected to the rectifier 226, which is connected to a low drop out regulator 228. The energy is received by the inductor 208 and transmitted to the rectifier 226, which converts the alternating current (AC) to direct current (DC). The low dropout regulator 228 regulates the voltage from the rectifier 226 forwards it to the charger 232 and outputs it to the battery 230.

Figure 3:
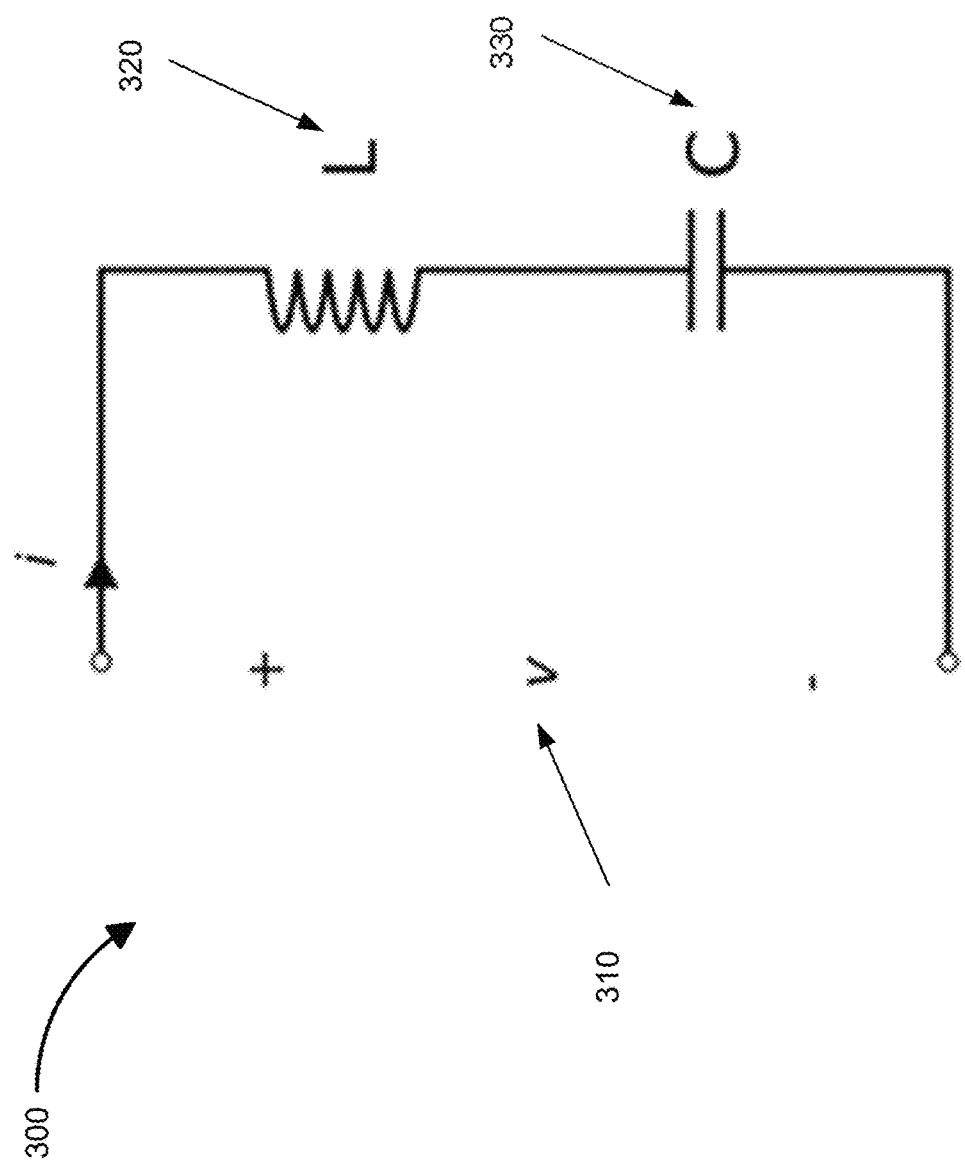
FIG. 3 is a diagram of basic components of a resonant circuit or an LC circuit, consistent with exemplary embodiments of the present disclosure.

FIG. 3 shows basic components of a resonant circuit or an LC circuit, consistent with exemplary embodiments of the present disclosure. Voltage input from the transformer is shown as v 310. L is the inductor 320 that is connected in series to a capacitor C 330. An LC circuit is also known as a tuned circuit. An LC circuit acts as an electrical resonator storing energy oscillating at the circuit's resonant frequency.

Figure 4:
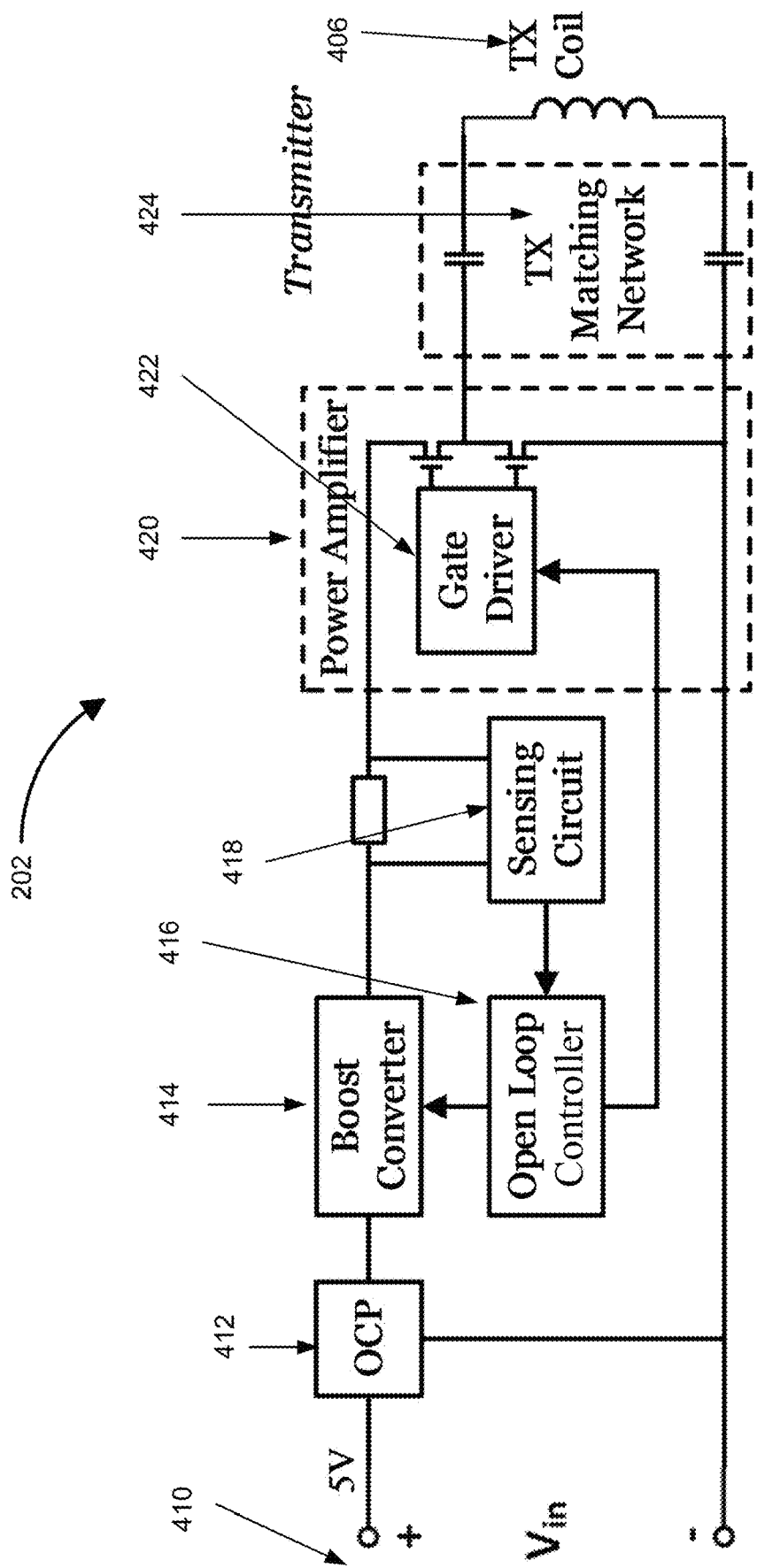
FIG. 4 is a diagram of a wireless charging transmitter, consistent with exemplary embodiments of the present disclosure.

FIG. 4 shows the transmitter side 202 of the wireless charging system 200, consistent with exemplary embodiments of the present disclosure. As shown in FIG. 4, the transmitter side 202 is coupled by inductor TX Coil 406. In one exemplary embodiment, the transmitter side 202 includes voltage input nodes (+ and −) 410, an over current protection circuit OCP 412, a boost converter 414, an open loop controller 416, a sensing circuit 418, a power amplifier 420 with a gate driver 422 and a transmitter matching network 424.

As shown in FIG. 4, the input nodes receive an input voltage Vin 410. In certain embodiments, the input voltage Vin is 5 volts. The input voltage Vin is connected to an over current protection circuit 412. The input nodes are connected to a boost converter 414. The boost converter 414 can provide a range of the DC voltage that can be fed into the power amplifier. For example, the boost converter 414 may be a step up converter that converts the Vin 410 from 5 volts to 12 volts. The output of the boost converter 414 feeds the power amplifier 420, which amplifies the input voltage Vin. The power amplifier 420 is connected to the TX matching network 424. The transmission is shown as power-line communication in FIG. 4.

Open loop controller 416 is connected to the gate driver 422 and the boost converter 414. The gate driver 422 acts as a switch to turn on or off the power amplifier 420. The power amplifier 420 may be periodically turned on and off to check for any power receiver device. To conserve power, the power amplifier 420 may repeatedly turn on for a very short period, e.g., a few seconds, when RX is unloaded. When one or more electric devices are detected, the power amplifier 420 may stayed turned on through the gate driver 422. When there is no electric device on the receiver side, the power amplifier 420 is turned off using the gate driver 422.

The sensing circuit 418 gives feedback to the gate driver 422 through the open loop controller 416. The sensing circuit 418 detects whether there are one or more electric devices 110 placed in the cup holder 120 for charging. The open loop controller 416 gives feedback to the boost converter 414 as well. The sensing circuit 418 working together with the open loop controller 416 optimizes charging efficiency based on real-time monitoring of system parameters from the sensing circuit 418. The unloaded power consumption, i.e., the power consumption when there are no electric devices charging, may be as low as or under 0.5 watts.

The TX matching network 424 is connected to the inductor 406. The TX matching network 424 may include one or more capacitors. Capacitance of one or more of the capacitors may be adjustable. The TX matching network 424 and the inductor 406 form a transmitter resonant circuit or an LC circuit where L represents the inductor and C represents the capacitor connected together. The frequency of the LC circuit can be adjusted by adjusting the capacitance of the TX matching network 424. The inductor 406 transmits the energy to an inductor on the receiver side.

Figure 5:
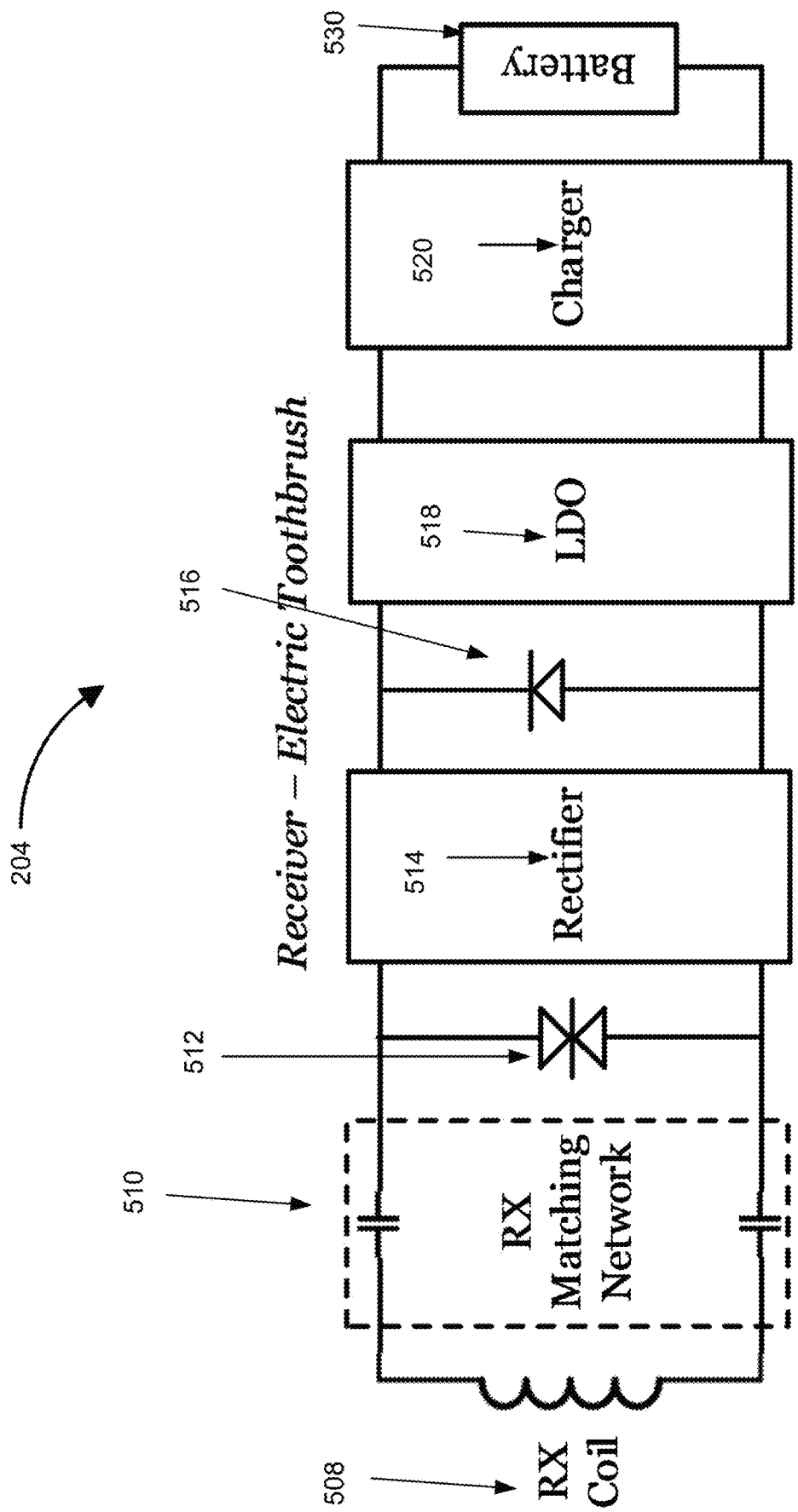
FIG. 5 is a diagram of a wireless charging receiver, consistent with exemplary embodiments of the present disclosure.

FIG. 5 shows the receiver side 204 of the wireless charging system 200, consistent with exemplary embodiments of the present disclosure. The receiver side 204 includes a receiver matching network 510, a rectifier 514, a low dropout regulator 518, a charger 520 and a battery 530. In certain embodiments, the receiver side includes a back to back transient-voltage-suppression diodes 512 before the rectifier 512 and a Zener diode 516 after the rectifier to protect the system from transient high voltages. In certain embodiments, the low dropout regulator 518 may be replaced by a buck converter.

On the receiver side 204, similar to the transmitter side 202, the inductor 508 is connected to the RX matching network 510, which has one or more capacitors. One or more of the capacitors may have adjustable capacitance. The capacitors are used to adjust the frequency of an LC circuit formed by the inductor 508 and RX matching network 510. The RX matching network 510 and the inductor 508 form a receiver resonant circuit. The RX matching network 510 is connected to the rectifier 514, which is connected to a low drop out regulator 518. The energy is received by the inductor 508 and transmitted to the rectifier 514, which converts the alternating current (AC) to direct current (DC). The low dropout regulator 518 regulates and outputs the voltage to the charger 520 that outputs the voltage to the battery 530 for charging.

Figure 6:
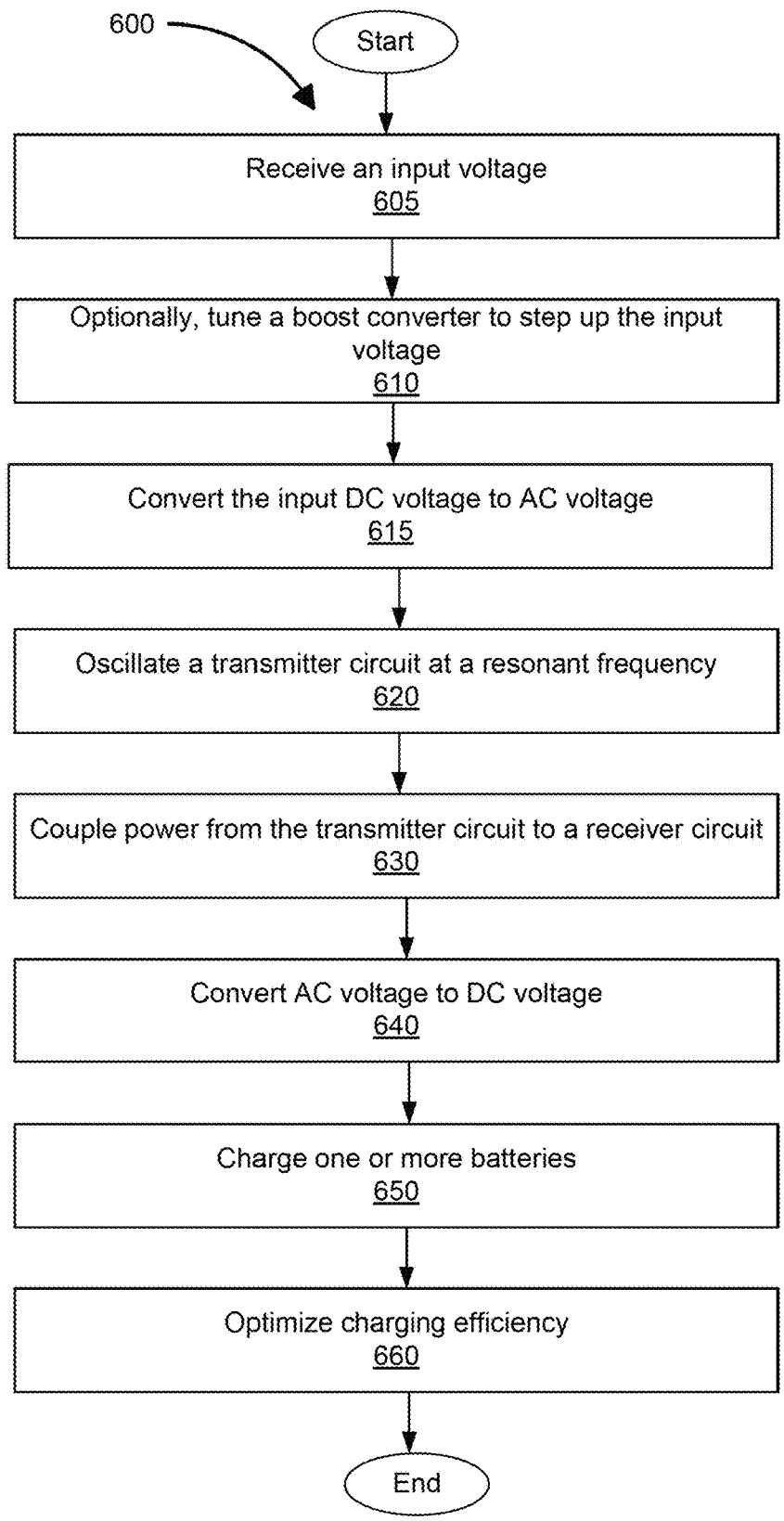
FIG. 6 is a flowchart illustrating a method for charging electric devices, consistent with exemplary embodiments of the present disclosure.

FIG. 6 is a flowchart illustrating a method 600 for wireless electrical charging, consistent with exemplary embodiments of the present disclosure. Method 600 may include a number of steps, some of which may be optional. The steps may also be rearranged in another order.

In Step 605, one or more components of the wireless charging system 100 (or system 200), e.g., the input nodes 410, may receive an input voltage. The input voltage may be a DC voltage received from a charger. In some embodiments, the DC voltage is provided using a USB port. In some embodiments, the DC voltage supplied is 5 volts. In some embodiments, the DC voltage supplied is 12 volts.

In some embodiments, in optional step 610, one or more components of the wireless charging system 100, e.g., the boost converter 414, may step up the input voltage supplied in step 605 to 12 volts or any other desired voltage level using a boost converter.

In Step 615, one or more components of the wireless charging system 100, e.g., the power amplifier 420, may convert the DC voltage to an AC voltage.

In Step 620, one or more components of the wireless charging system 100, e.g., the transmitter resonant circuit, may oscillate at a resonant frequency.

In Step 630, one or more components of the wireless charging system 100, e.g., the receiver resonant circuit, may oscillate at a resonant frequency. For example, power can be inductively coupled from the TX coil 406 to the RX coil 506, and the component(s) performing the step 620 can be physically separated from the component(s) performing the step 630.

In Step 640, one or more components of the wireless charging system 100, e.g., the rectifier 514, may convert the AC voltage to a DC voltage.

In Step 650, one or more components of the wireless charging system 100, e.g., the RX matching network 510 and the RX coil 506 or a corresponding resonant circuit, may charge one or more batteries in the electric devices. The one or more electric devices can be placed in a free position with adjustable distance and adjustable angle. Thus, the one or more electrical devices can be wireless.

In Step 660, one or more components of the wireless charging system 100 may optimize the charging efficiency. For example, the resonant frequency ω=w, may be adjusted to maximize the power transfer efficiency η described above. The resonant frequency may be adjusted by tuning/adjusting the capacitor or inductor in the transmitter and/or receiver LC circuit. For another example, open loop controller 416 may enable charging when the one or more electric devices are placed on the holder, and disable charging when the holder is empty. Thus, the wireless charging described above based on system 100 can optimize its charging efficiency.

Figure 7:
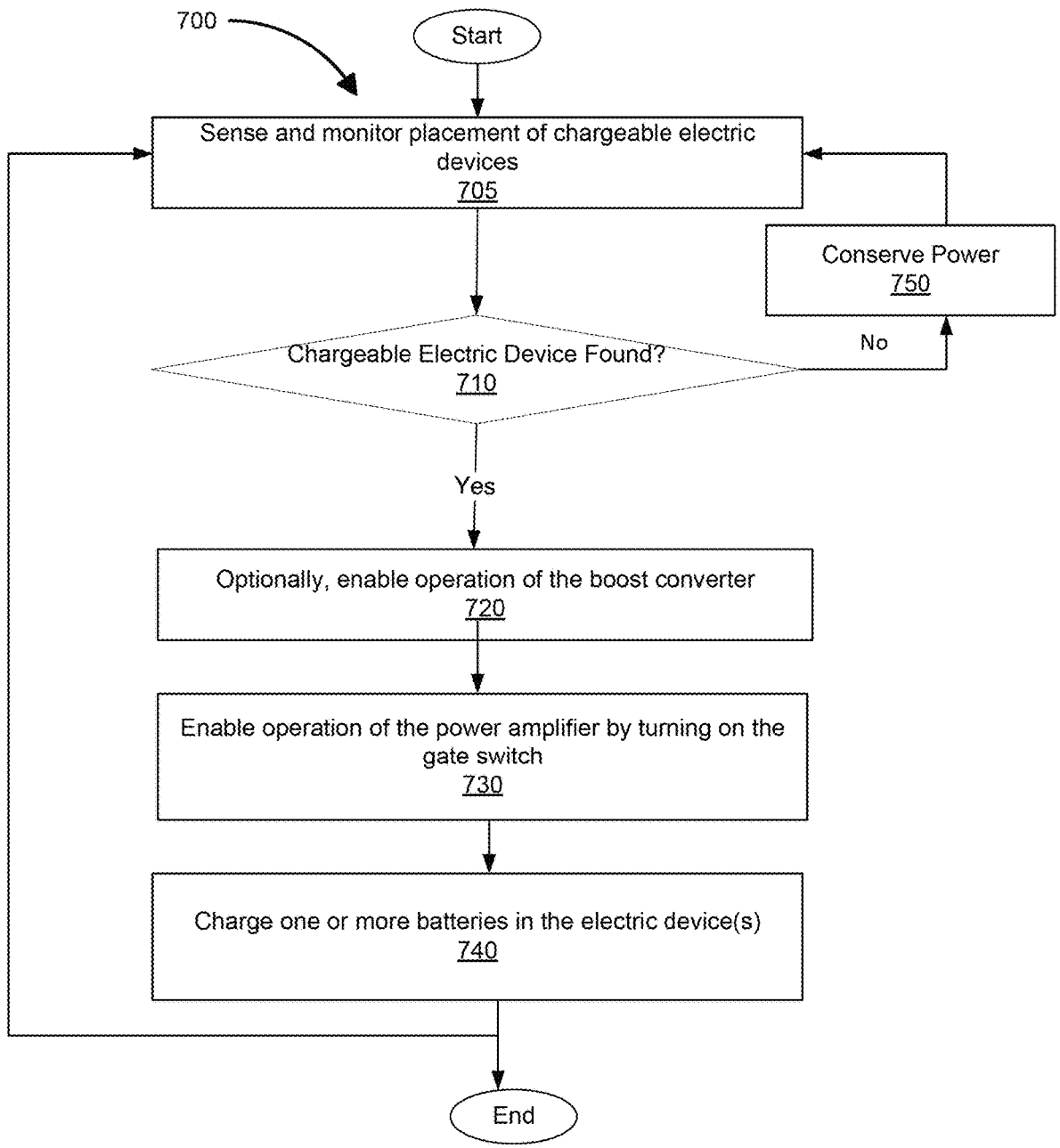
FIG. 7 is a flowchart illustrating a method for charging electric devices using a sensing circuit, consistent with exemplary embodiments of the present disclosure.

FIG. 7 is a flowchart illustrating a method 700 for wireless electrical charging, consistent with exemplary embodiments of the present disclosure. Method 700 may include a number of steps, some of which may be optional. The steps may also be rearranged in another order. For example, steps 720 and 730 may be performed in either order or concurrently.

In Step 705, one or more components of the wireless charging system 100 (or system 200) sense and monitor the placement of chargeable electric devices. In Step 710, the decision of whether a chargeable electric device is found is examined. If a chargeable electric device is not found, in Step 750, the wireless charging system 100 conserves power by turning on and off electric components, e.g., power amplifier 420, repeatedly for electric device detection. If a chargeable electric device is found, one or more components of the wireless charging system 100 are enabled for operation. In some embodiments, at optional step 720, one or more components of the wireless charging system 100, e.g., the boost converter 414, steps up the input voltage supplied from 5 volts to 12 volts or any desired voltage level. In Step 730, one or more components of the wireless charging system 100, e.g., the gate driver 422, enables operation of the power amplifier by turning on the gate switch. In Step 740, one or more components of the wireless charging system 100 charge one or more batteries in the electric devices. The wireless charging system 100 continues to sense and monitor placement of chargeable electric devices in real-time.

Another aspect of the disclosure is directed to a non-transitory computer-readable storage medium storing instructions which, when executed, cause one or more processors to perform the method, as discussed above. The computer-readable storage medium may include volatile or non-volatile, magnetic, semiconductor, tape, optical, removable, non-removable, or other types of computer-readable storage medium or computer-readable storage devices. For example, the computer-readable storage medium may be the storage unit or the memory module having the computer instructions stored thereon, as disclosed. In some embodiments, the computer-readable storage medium may be a disc or a flash drive having the computer instructions stored thereon.

A person skilled in the art can further understand that, various exemplary logic blocks, modules, circuits, and algorithm steps described with reference to the disclosure herein may be implemented as specialized electronic hardware, computer software, or a combination of electronic hardware and computer software. For examples, the modules/units may be implemented by one or more processors to cause the one or more processors to become one or more special purpose processors to executing software instructions stored in the computer-readable storage medium to perform the specialized functions of the modules/units.

The flowcharts and block diagrams in the accompanying drawings show system architectures, functions, and operations of possible implementations of the system and method according to multiple embodiments of the present invention. In this regard, each block in the flowchart or block diagram may represent one module, one program segment, or a part of code, where the module, the program segment, or the part of code includes one or more executable instructions used for implementing specified logic functions. It should also be noted that, in some alternative implementations, functions marked in the blocks may also occur in a sequence different from the sequence marked in the drawing. For example, two consecutive blocks actually can be executed in parallel substantially, and sometimes, they can also be executed in reverse order, which depends on the functions involved. Each block in the block diagram and/or flowchart, and a combination of blocks in the block diagram and/or flowchart, may be implemented by a dedicated hardware-based system for executing corresponding functions or operations, or may be implemented by a combination of dedicated hardware and computer instructions.

As will be understood by those skilled in the art, embodiments of the present disclosure may be embodied as a method, a system or a computer program product. Accordingly, embodiments of the present disclosure may take the form of an entirely hardware embodiment, an entirely software embodiment or an embodiment combining software and hardware for allowing specialized components to perform the functions described above. Furthermore, embodiments of the present disclosure may take the form of a computer program product embodied in one or more tangible and/or non-transitory computer-readable storage media containing computer-readable program codes. Common forms of non-transitory computer readable storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM or any other flash memory, NVRAM, a cache, a register, any other memory chip or cartridge, and networked versions of the same.

Embodiments of the present disclosure are described with reference to flow diagrams and/or block diagrams of methods, devices (systems), and computer program products according to embodiments of the present disclosure. It will be understood that each flow and/or block of the flow diagrams and/or block diagrams, and combinations of flows and/or blocks in the flow diagrams and/or block diagrams, can be implemented by computer program instructions. These computer program instructions may be provided to a processor of a computer, an embedded processor, or other programmable data processing devices to produce a special purpose machine, such that the instructions, which are executed via the processor of the computer or other programmable data processing devices, create a means for implementing the functions specified in one or more flows in the flow diagrams and/or one or more blocks in the block diagrams.

These computer program instructions may also be stored in a computer-readable memory that can direct a computer or other programmable data processing devices to function in a particular manner, such that the instructions stored in the computer-readable memory produce a manufactured product including an instruction means that implements the functions specified in one or more flows in the flow diagrams and/or one or more blocks in the block diagrams.

These computer program instructions may also be loaded onto a computer or other programmable data processing devices to cause a series of operational steps to be performed on the computer or other programmable devices to produce processing implemented by the computer, such that the instructions (which are executed on the computer or other programmable devices) provide steps for implementing the functions specified in one or more flows in the flow diagrams and/or one or more blocks in the block diagrams. In a typical configuration, a computer device includes one or more Central Processing Units (CPUs), an input/output interface, a network interface, and a memory. The memory may include forms of a volatile memory, a random access memory (RAM), and/or non-volatile memory and the like, such as a read-only memory (ROM) or a flash RAM in a computer-readable storage medium. The memory is an example of the computer-readable storage medium.

The computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The computer-readable medium includes non-volatile and volatile media, and removable and non-removable media, wherein information storage can be implemented with any method or technology. Information may be modules of computer-readable instructions, data structures and programs, or other data. Examples of a non-transitory computer-readable medium include but are not limited to a phase-change random access memory (PRAM), a static random access memory (SRAM), a dynamic random access memory (DRAM), other types of random access memories (RAMs), a read-only memory (ROM), an electrically erasable programmable read-only memory (EEPROM), a flash memory or other memory technologies, a compact disc read-only memory (CD-ROM), a digital versatile disc (DVD) or other optical storage, a cassette tape, tape or disk storage or other magnetic storage devices, a cache, a register, or any other non-transmission media that may be used to store information capable of being accessed by a computer device. The computer-readable storage medium is non-transitory, and does not include transitory media, such as modulated data signals and carrier waves.

The specification has described methods, apparatus, and systems for wireless electrical charging. The illustrated steps are set out to explain the exemplary embodiments shown, and it should be anticipated that ongoing technological development will change the manner in which particular functions are performed. Thus, these examples are presented herein for purposes of illustration, and not limitation. For example, steps or processes disclosed herein are not limited to being performed in the order described, but may be performed in any order, and some steps may be omitted, consistent with the disclosed embodiments. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

It will be appreciated that the present invention is not limited to the exact construction that has been described above and illustrated in the accompanying drawings, and that various modifications and changes can be made without departing from the scope thereof. It is intended that the scope of the invention should only be limited by the appended claims.

What is claimed is:
1. A system for charging one or more electric devices, the system comprising:
   a charging station comprising:
      an input node configured to receive a power input;
      a boost converter coupled to the input node and configured to step up the power input to a boosted voltage level;

a sensing circuit coupled to the boost converter and configured to detect an electronic device at a receiver side after the power input has been stepped up by the boost converter;

a power amplifier coupled to the sensing circuit, and a switch coupled to the power amplifier to turn on and off the power amplifier intermittently to allow a detection of the electronic device at the receiver side, wherein the boost converter is configured to provide a range of DC voltage to the power amplifier, and the electronic device is detected by the sensing circuit; and a transmitter resonant circuit coupled to the power amplifier and including a transmitter coupling coil configured to oscillate at a resonant frequency; and the one or more electric devices to be placed at the receiver side, comprising:

a receiver resonant circuit including a receiver coupling coil configured to be wirelessly coupled to the transmitter coupling coil; and a DC voltage charger configured to charge one or more batteries in the electric device.

2. The system of claim 1, wherein the resonant frequency is between 1 to 10 MHz.

3. The system of claim 2, wherein:

the transmitter resonant circuit is coupled to the receiver resonant circuit with a corresponding coupling efficiency smaller than 0.1.

4. The system of claim 1, wherein the charging station further comprises a holder configured to hold the one or more electric devices at free positions covering an adjustable distance and an adjustable angle with respect to the transmitter coupling coil.

5. The system of claim 4, wherein the wireless transmitter resonant circuit is on a plate separate from a base of the holder.

6. The system of claim 1, wherein the power input is a fixed input DC voltage supplied to the input node using a USB port.

7. The system of claim 4, wherein turning on and off the power amplifier intermittently to allow a detection of the electronic device at a receiver side comprises:

providing, by the sensing circuit, a detection result to an open loop controller; and turning on and off the power amplifier intermittently by the open loop controller.

8. The system of claim 1, wherein the one or more electric devices comprises a rectifier coupled to the receiver resonant circuit and at least one of:

a back to back transient voltage suppression diode placed before the rectifier; or a Zener diode placed after the rectifier.

9. A method for charging one or more electric devices, the method comprising:

receiving a power input by a charging station;

stepping up, by a boost converter, the power input to a boosted voltage;

amplifying the boosted voltage through a power amplifier, wherein the boost converter is configured to provide a range of DC voltage to the power amplifier;

turning on and off the power amplifier intermittently to allow a detection of an electronic device at a receiver side, wherein the electronic device is detected by a sensing circuit;

if one or more electronic device is detected at the receiver side, oscillating a transmitter resonant circuit of the charging station at a resonant frequency; and wirelessly coupling the transmitter resonant circuit to a receiver resonant circuit of the one or more electric devices.

10. The method of claim 9, wherein the resonant frequency is between 1 to 10 MHz.

11. The method of claim 10, wherein:

the transmitter resonant circuit is coupled to the receiver resonant circuit with a corresponding coupling efficiency smaller than 0.1.

12. The method of claim 9, further comprising holding the one or more electric devices in a holder of the charging station at free positions covering an adjustable distance and an adjustable angle with respect to the transmitter resonant circuit.

13. The method of claim 12, wherein the wireless transmitter resonant circuit is on a plate separate from a base of the holder.

14. The method of claim 9, further comprising supplying a fixed input DC voltage using a USB port as the power input.

15. The method of claim 12, wherein turning on and off the power amplifier intermittently to allow a detection of an electronic device at a receiver side comprises:

providing, by the sensing circuit, a detection result to an open loop controller;

turning on and off the power amplifier intermittently by the open loop controller.

16. The method of claim 9, wherein the receiver resonant circuit comprises a rectifier and at least one of a back to back transient voltage suppression diode before the rectifier or a Zener diode after the rectifier.

* * * * *